United States Patent [19]

Fisher et al.

[11] Patent Number: 5,302,711
[45] Date of Patent: Apr. 12, 1994

[54] ESTER CLEAVAGE PROCESS FOR USE WITH β-LACTAMS

[75] Inventors: Jack W. Fisher; Kristina Thomas, both of Indianapolis, Ind.

[73] Assignee: Eli Lilly and Company, Indianapolis, Ind.

[21] Appl. No.: 836,640

[22] Filed: Feb. 18, 1992

[51] Int. Cl.$^5$ .................. C07D 499/08; C07D 501/04
[52] U.S. Cl. .................... 540/215; 540/205; 540/222; 540/225; 540/227; 540/310
[58] Field of Search ............. 540/225, 230, 222, 215, 540/310, 205, 227

[56] References Cited

U.S. PATENT DOCUMENTS

| | | | |
|---|---|---|---|
| 5,043,439 | 8/1991 | Kant et al. | 540/215 |
| 5,095,107 | 3/1992 | Blanchard | 540/205 |
| 5,246,926 | 9/1993 | Bateson et al. | 540/222 |

OTHER PUBLICATIONS

March, J., *Advanced Organic Chemistry, Reactions, Mechanisms, and Structure*, 3rd ed., p. 386, (1985).
Dean, P. D. G., "Halogenolysis of Methyl Glycyrrhetate with Lithium Iodide-Dimethylformamide," J. Chem. Soc., p. 6655, (1965).
McMurry, J. E. and Wong, G. B., "An improved method for the cleavage of methyl esters," Synthetic Communications, 2(6), 389–394 (1972).
Mochida, K. and Hirata, T., "Synthetic Studies on 1-Carbacephem Antibiotics: New Synthetic approach to 3H-Carbacephems," Chem. Pharm. Bull., 36(9), 3642–3645, (1988).
Martinez, A. G., Barcina, J. O., del Veccio, H., Hanack, M. and Subramanian, L. R., "Non-hydrolytic Cleavage of Esters with Magnesium Iodide in Aprotic Non-polar Solvents," Tetrahedron Letters, 32 (42) 5931–5934 (1991).
Olsher, U., Izatt, R. M., Bradshaw, J. S., Dalley, N. K., "Coordination Chemistry of Lithium Ion: A Crystal and Molecular Structure Review," Chem. Rev., 91, 137–164, (1991).

*Primary Examiner*—Nicholas S. Rizzo
*Attorney, Agent, or Firm*—Janet T. McClain; Leroy Whitaker

[57] ABSTRACT

The present invention provides a novel ester cleavage process for use with β-lactams. The process is useful because of mild conditions necessary to complete the reaction, such conditions being especially suitable for β-lactams.

18 Claims, No Drawings

ESTER CLEAVAGE PROCESS FOR USE WITH β-LACTAMS

BACKGROUND OF THE INVENTION

This invention belongs to the field of organic chemistry and the synthesis of antibiotics. The invention provides a method for the removal of a carboxy-protecting group from cephalosporin, carbacephalosporin, penicillin and azetidin-2 one carboxylic acids using mild conditions. The carboxy group is desirably protected during the preparation of these compounds to block or prevent the otherwise reactive acidic carboxy group from participating in reactions that are in competition with a desired reaction at another site in the molecule. The esters are convenient and economical to handle in chemical processing but must eventually be removed, because the compounds are used as antibiotics in either the acid or salt form. The ability to remove the carboxy-protecting group under mild conditions is useful because of the sensitivity of these β-lactam compounds to heat, acidity and basicity.

The preparation of cephalosporins is taught broadly by Chauvette, U.S. Pat. No. 4,064,343. The preparation of 1-carbacephalosporins is taught broadly by Christensen, et al., in U.S. Pat. No. 4,226,866 and Munroe, in U.S. Pat. No. 4,791,106. The preparation of penicillins is taught by J. C. Sheehan and G. D. Laubach, (1951) J. Am. Chem. Soc., 73: 4376; J. C. Sheehan and E. J. Corey, (1951), J. Am. Chem. Soc., 73: 4756; J. C. Sheehan and G. D. Laubach, (1951), J. Am. Chem. Soc., 73: 4752. The preparation of azetidin-2-ones is taught broadly in Evans, et al. in U.S. Pat. No. 4,665,171.

SUMMARY OF THE INVENTION

This invention provides a process for producing a compound of the formula I

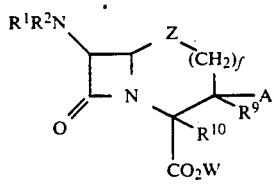

or a pharmaceutically acceptable salt thereof; which comprises reacting, in a non-basic solvent having a dielectric constant between about 0 and about 15, lithium iodide and a compound of the formula II or a salt of a compound of the formula II that is capable of forming a salt,

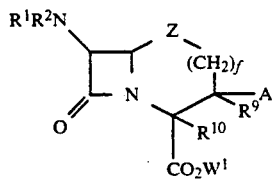

wherein:
W is lithium ion;
$W^1$ is a carboxy-protecting group;
Z is —S—, —S(O)—, —SO$_2$— or —CH$_2$—;
$R^9$ is hydrogen, $C_1$–$C_6$ alkyl or is combined with $R^{10}$ to form a double bond;

$R^{10}$ is hydrogen or is combined with $R^9$ to form a double bond; f is 0 or 1, with the provisos that when f is 1, $R^9$ and $R^{10}$ combine to form a double bond and when f is 0, A is $C_1$–$C_6$ alkyl;

$R^1$ and $R^2$ are independently hydrogen, $C_1$–$C_6$ alkyl, amino-protecting group or —C(O)—R where R is the residue of a carboxylic acid, with the proviso that when one of $R^1$ or $R^2$ is —C(O)—R then the other cannot be hydrogen;

A is hydrogen or a substituent selected from those found in the cephalosporin, 1-carbacephalosporin or penicillin arts.

Typical A substituents include hydrogen, halo, cyano, hydroxy, azido, $C_1$–$C_6$ alkyl, halo($C_1$–$C_6$)alkyl, cyano-($C_1$–$C_6$) alkyl, $C_1$–$C_6$ alkylthio, $C_1$–$C_6$ alkoxy, trifluoromethanesulfonyloxy or a group of the formula —C(O)—$R^3$, where $R^3$ is hydroxy, halo, azido, $C_1$–$C_6$ alkoxy, 2-[tri-($C_1$–$C_4$)alkylsilyl]ethoxy, $C_2$–$C_6$ alkenoxy, $C_2$–$C_6$ alkynyloxy, $C_1$–$C_4$ alkoxycarbonyloxy, phenoxy, or substituted phenoxy;

or $R^3$ is $C_1$–$C_6$ alkoxy substituted by one or two of the same or different groups selected from among hydroxy, amino, $C_1$–$C_4$ alkylamino, di($C_1$–$C_4$)alkylamino, $C_1$–$C_4$ alkanoylamino, halo, $C_1$–$C_4$ alkoxy, $C_1$–$C_4$ alkylthio, cyano, carboxy, $C_1$–$C_4$ alkoxycarbonyl, carbamoyl, carbamoyloxy, N-($C_1$–$C_4$)alkylcarbamoyloxy, N,N-di($C_1$–$C_4$)-alkylcarbamoyloxy, $C_1$–$C_4$ alkoxycarbonyloxy, phenoxycarbonyloxy, $C_1$–$C_4$ alkoxycarbonylamino, phenoxycarbonylamino, N-($C_1$–$C_4$)alkylcarbamoylamino, N,N-di($C_1$–$C_4$)alkylcarbamoylamino, N-phenylcarbamoylamino, anilino, substituted anilino, phenyl, substituted phenyl or a heterocyclic amino group of the formula —NHR$^4$, where R$^4$ is thienyl, furyl or a 5-membered nitrogen-containing heterocyclic ring represented by the formulae

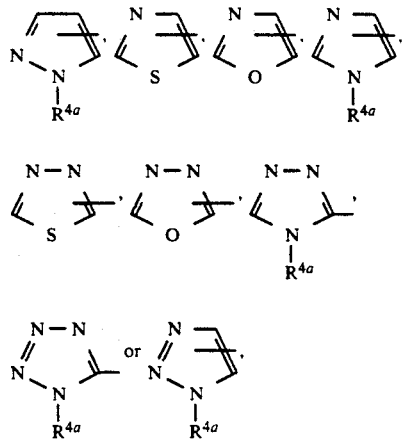

where $R^{4a}$ is hydrogen, $C_1$–$C_4$ alkyl or $C_1$–$C_4$ alkyl substituted by carboxy, sulfo or di($C_1$–$C_4$)alkylamino, or $R^4$ is a 6-membered nitrogen-containing ring represented by the formulae

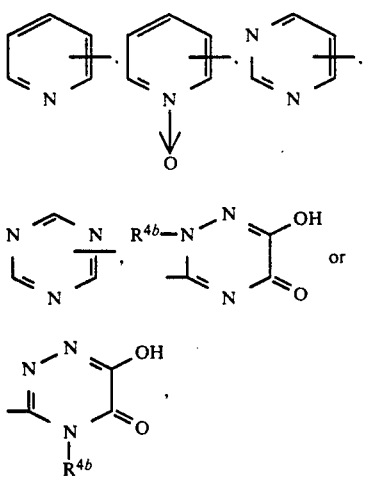

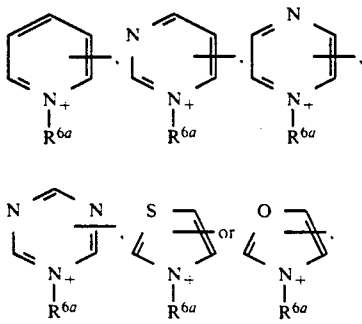

where $R^{4b}$ is hydrogen or $C_1$-$C_4$ alkyl, or a heterocyclic thio group of the formula —$SR^5$, where $R^5$ is phenyl, substituted phenyl or $R^4$ as defined above;

or a quaternary heterocyclic group of the formula $X\ominus R^6\oplus$—, where $R^6\oplus$ is a nitrogen-containing heterocyclic represented by the formulae where $R^{6a}$ is $C_1$-$C_4$ alkyl, benzyl or $CH_2COCH_3$; and $X\ominus$ halide, sulfate or nitrate anion;

or a heterocyclic group of the formula $X\ominus R^6\oplus$—S—, where $R^6\oplus$ and $X\ominus$ are as defined above;

or a heterocyclic group $R^4$ as defined above;

or $R^3$ is an amino group represented by the formula —$NR^{3a}R^{3b}$, where $R^{3a}$ and $R^{3b}$ are independently hydrogen, phenyl, substituted phenyl, $C_1$-$C_4$ alkyl, or $C_1$-$C_4$ alkyl substituted by one or two of the same or different groups selected from among halo, hydroxy, $C_1$-$C_4$ alkanoyloxy, $C_1$-$C_4$ alkylsulfonyloxy, phenyl, substituted phenyl, amino, or $C_1$-$C_4$ alkanoylamino;

or $R^{3a}$ and $R^{3b}$ are taken together with the nitrogen atom to which they are bonded to form a 5-7 membered ring represented by the formula

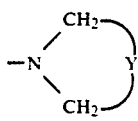

where Y is (—$CH_2$—)$_p$ or —$CH_2$—$Y^1$—$CH_2$— where p is 2, 3 or 4 and $Y^1$ is —O—, —S— or —$N(R^{3c})$— where $R^{3c}$ is hydrogen or $C_1$-$C_4$ alkyl;

or $R^{3a}$ is hydrogen and $R^{3b}$ is $C_1$-$C_4$ alkyl substituted by a heterocyclic $R^4$, a heterocyclic amino group —$NHR^4$, a heterocyclic thio group —$SR^4$ or a quaternary heterocyclic group $X\ominus R^6\oplus$—, where $R^4$, $R^6\oplus$ and $X\ominus$ are as defined above;

or $R^3$ is phenyl, substituted phenyl or a heterocyclic amino group —$NHR^4$, where $R^4$ is as defined above;

or $R^3$ is $C_1$-$C_4$ alkyl or $C_1$-$C_4$ alkyl substituted by hydroxy, $C_1$-$C_4$ alkanoyloxy, $C_1$-$C_4$ alkoxy, $C_1$-$C_4$ alkylthio, halo, carboxy, cyano, amino, $C_1$-$C_4$ alkylamino, di($C_1$-$C_4$)alkylamino, $C_1$-$C_4$ alkanoylamino, $C_1$-$C_4$ alkylsulfonylamino, $C_1$-$C_4$ alkylsulfonyloxy, phenyl, substituted phenyl, phenylthio, substituted phenylthio, phenoxy, substituted phenoxy, anilino, substituted anilino, a heterocyclic group $R^4$, a heterocyclic amino group —$NHR^4$, a heterocyclic thio group —$SR^4$ or a quaternary heterocyclic group $X\ominus R^6\oplus$— or $X\ominus R^6\oplus$—S—, where $R^4$, $R^6\oplus$, and $X\ominus$ are as defined above;

or $R^3$ is phenyl, thienyl, furyl, pyridyl, pyrimidyl, imidazolyl, pyrazolyl, tetrazolyl, oxazolyl, thiazolyl, thiadiazolyl or oxadiazolyl or said phenyl or heterocycle substituted by one or two of the same or different substituents selected from $C_1$-$C_4$ alkyl, $C_1$-$C_4$ alkoxy, halo, amino or hydroxy;

or $R^3$ is a carboxy group or a derivative of a carboxy group represented by the formula —$C(O)R^7$ where $R^7$ is hydrogen, hydroxy, $C_1$-$C_4$ alkoxy, phenoxy, substituted phenoxy, tri($C_1$-$C_4$)alkylsilyloxy, amino, $C_1$-$C_4$ alkylamino, di-($C_1$-$C_4$)alkylamino, phenyl, substituted phenyl or $C_1$-$C_4$ alkyl;

or $R^3$ is a group of the formula $X\ominus R^8\oplus$—$CH_2$ where $x\ominus$ is as defined above and $\oplus R^8$ is pyridinium or pyridinium substituted by one or two of the same or different groups selected from among $C_1$-$C_4$ alkyl, $C_1$-$C_4$ alkoxy, $C_1$-$C_4$ alkylthio, hydroxy, halo, trifluoromethyl, cyano, carboxy, carbamoyl, amino or $C_1$-$C_4$ alkoxycarbonyl;

or $\oplus R^8$ is pyridinium substituted on the adjacent carbon atoms with a divalent alkylene group represented by the formula (—$CH_2$—)$_q$ where q is 3, 4 or 5, or the divalent alkylene group is interrupted by an oxygen, sulfur or one or two nitrogen atoms and in addition can contain one or two double bonds and can be substituted in either ring by one or two of the same or different substituents selected from the groups defined above when $\oplus R^8$ is a substituted pyridinium;

or $\oplus R^8$ is thiazolium or a thiazolium substituted by one or two of the same or different groups selected from among amino, $C_1$-$C_4$ alkyl, $C_1$-$C_4$ alkylthio, $C_1$-$C_4$ alkoxy or $C_1$-$C_4$ alkyl substituted by hydroxy, $C_1$-$C_4$ alkanoyloxy, $C_1$-$C_4$ alkylsulfonyloxy, halo, $C_1$-$C_4$ alkoxy, $C_1$-$C_4$ alkylthio or amino;

or $\oplus R^8$ is thiazolium substituted on the adjacent carbon atoms with a divalent alkylene group represented by the formula (—$CH_2$—)$_q$ where q is 3,4 or 5.

This invention also relates to a process for producing a compound of the formula III

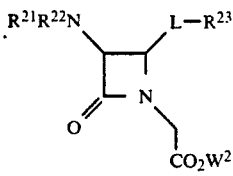

III or a pharmaceutically acceptable salt thereof; which comprises reacting, in a non-basic solvent having a dielectric constant between about 0 and about 15, lithium iodide and a compound of the formula IV or a salt of a compound of the formula IV that is capable of forming a salt,

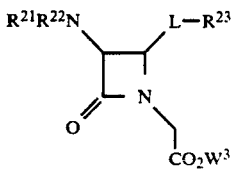

IV wherein:

$W^2$ is lithium ion;

$W^3$ is a carboxy-protecting group;

$R^{21}$ and $R^{22}$ are independently selected from among hydrogen, $C_1$–$C_6$ alkyl, amino-protecting group or —C(O)—R where R is the residue of a carboxylic acid, with the proviso that when one of $R^{21}$ and $R^{22}$ is —C(O)—R then the other cannot be hydrogen;

L is —$CH_2$—$CH_2$— or —CH=CH—;

and $R^{23}$ is phenyl, phenyl($C_1$–$C_6$)alkyl, phenyl($C_1$–$C_6$)-alkoxy, halophenyl, furyl or naphthyl.

DETAILED DESCRIPTION OF THE INVENTION

The compounds prepared by the process of this invention are known in the β-lactam art. To assure that the reader understands the compounds, and understands the esters which are the starting compounds used in the present invention, some discussion and explanation of the formulae will be given.

In the above general formulae, various generalized terms are used to describe the numerous groups. The generalized terms have their usual meanings in organic chemistry. All temperatures stated herein are in degrees Celsius. All units of measurement employed herein are in weight units except for liquids, which are in volume units.

The term ∓$C_1$–$C_6$ alkyl represents a straight or branched alkyl chain having from one to six carbon atoms. Typical $C_1$–$C_6$ alkyl groups include methyl, ethyl, propyl, isopropyl, butyl, isobutyl, sec-butyl, tert-butyl, pentyl, neopentyl, hexyl, and the like. The term "$C_1$–$C_6$ alkyl" includes within its definition the terms "$C_1$–$C_4$ alkyl" and "$C_1$–$C_3$ alkyl.

"Halo" represents chloro, fluoro, bromo or iodo.

"$C_1$–$C_4$ alkoxycarbonyl" represents a straight or branched chain alkoxy group having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, isobutoxy, sec-butoxy, tert-butoxy, pentoxy, neopentoxy, hexoxy, and the like. The term "$C_1$–$C_6$ alkoxy" includes within its definition the term "$C_1$–$C_4$ alkoxy".

"$C_1$–$C_4$ alkoxycarbonyloxy" represents a straight or branched chain alkoxy group having from one to four carbon atoms attached to a carbonyloxy moiety. Typical $C_1$–$C_4$ alkoxycarbonyloxy groups include methoxycarbonyloxy, ethoxycarbonyloxy, propoxycarbonyloxy, isopropoxycarbonyloxy, butoxycarbonyloxy and the like.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio, isobutylthio, sec-butylthio, tert-butylthio, pentylthio, neopentylthio, hexylthio and the like. The term "$C_1$–$C_6$ alkylthio" includes within its definition the term "$C_1$–$C_4$ alkylthio".

"Halo($C_1$–$C_6$)alkyl" represents a straight or branched alkyl chain having from one to six carbon atoms with from one to six halogen atoms attached to it. Typical halo($C_1$–$C_6$)alkyl groups include chloromethyl, trifluoromethyl, 2-bromoethyl, 1-chloroisopropyl, 2-chloroisopropyl, 2-fluoropropyl, 3-bromobutyl, 3-chloroisobutyl, fluoro-t-butyl, 5-iodopentyl, 1,1-dichloroisopentyl, 6,6,6-tribromohexyl and the like. The term "halo($C_1$–$C_6$)alkyl" includes within its definition the term "halo($C_1$–$C_4$)alkyl".

"Cyano($C_1$–$C_6$)alkyl" represents a straight or branched alkyl chain having from one to six carbon atoms with a cyano group attached to it. Typical cyano($C_1$–$C_6$)alkyl groups include cyanomethyl, 2 cyanoethyl, 2-cyanopropyl, 1-cyanoisopropyl, 4-cyanobutyl, 3-cyanoisobutyl, cyano-tert-butyl, 4-cyanopentyl, 6-cyanohexyl and the like. The term "cyano($C_1$–$C_6$)alkyl" includes within its definition the term "cyano($C_1$–$C_4$)alkyl".

"$C_1$–$C_4$ alkylamino" represents a straight or branched alkylamino chain having from one to four carbon atoms attached to a nitrogen atom. Typical $C_1$–$C_4$ alkylamino groups include methylamino, ethylamino, propylamino, isopropylamino, butylamino, isobutylamino, sec-butylamino and the like.

"Di($C_1$–$C_4$)alkylamino" represents a straight or branched dialkylamino group having two alkyl chains of from one to four carbon atoms attached to a common nitrogen atom. Typical di($C_1$–$C_4$)alkylamino groups include dimethylamino, ethylmethylamino, methylisopropylamino, tert-butylisopropylamino, di-tert-butylamino and the like.

"$C_2$–$C_4$ alkenyl" represents a straight or branched alkenyl chain having from two to four carbon atoms. Typical $C_2$–$C_4$ alkenyl groups include ethenyl propenyl 2-methyl-1-propenyl, 1-butenyl, 2-butenyl and the like.

"$C_2$–$C_6$ alkenyloxy" represents a straight or branched alkenyl chain having from two to six carbon atoms attached to an oxygen atom. Typical $C_2$–$C_6$ alkenyloxy groups include ethenyloxy, propenyloxy, 2-propenyloxy, 3-methyl-1-propenyloxy, 1-butenyloxy, 3-pentenyloxy, 4-hexenyloxy and the like.

"$C_2$–$C_4$ alkynyl" represents a straight or branched alkynyl chain having from two to four carbon atoms. Typical $C_2$–$C_4$ alkynyl groups include ethynyl, 1-propynyl, 2-propynyl, 1-butynyl, 2-butynyl and the like.

"$C_2$–$C_6$ alkynyloxy" represents a straight or branched alkynyl chain having from two to six carbon atoms attached to an oxygen atom. Typical $C_2$–$C_6$ alkynyl groups include ethynyloxy, 1-propynyloxy, 2-propynyloxy, 1-butynyloxy, 2-pentynyloxy, 5-hexynyloxy and the like.

"$C_1$–$C_3$ alkylsulfonyl" represents a straight or branched chain alkyl group having from one to three carbon atoms attached to a sulfonyl moiety. Typical $C_1$–$C_3$ alkylsulfonyl groups include methylsulfonyl, ethylsulfonyl, propylsulfonyl and isopropylsulfonyl.

"$C_1$–$C_4$ alkylsulfonylamino" represents a straight or branched chain alkyl group having from one to four carbon atoms attached to a sulfonylamino moiety. Typical $C_1$–$C_4$ alkylsulfonylamino groups include methylsulfonylamino, ethylsulfonylamino, propylsulfonylamino, isopropylsulfonylamino, butylsulfonylamino, isobutylsulfonylamino, sec-butylsulfonylamino, and tert-butylsulfonylamino.

"$C_1$–$C_4$ alkanoyl" represents a straight or branched chain alkyl group having from one to four carbon atoms attached to a carbonyl moiety. Typical $C_1$–$C_4$ alkanoyl groups include ethanoyl, propanoyl, isopropanoyl, butanoyl, isobutanoyl, sec-butanoyl, tert-butanoyl, pentanoyl and the like.

"$C_1$–$C_4$ alkanoyloxy" represents a straight or branched chain alkyl group having from one to four carbon atoms attached to a carbonyloxy moiety. Typical $C_1$–$C_4$ alkanoyloxy groups include ethanoyloxy, propanoyloxy, isopropanoyloxy, butanoyloxy, isobutanoyloxy, sec-butanoyloxy, tert-butanoyloxy, pentanoyloxy and the like.

"$C_1$–$C_4$ alkanoylamino" represents a straight or branched chain alkyl group attached to a carbonylamino moiety. Typical $C_1$–$C_4$ alkanoylamino groups include ethanoylamino, propanoylamino, isopropanoylamino, butanoylamino, isobutanoylamino, sec-butanoylamino, tert-butanoylamino, pentanoylamino and the like.

"N-($C_1$–$C_4$)alkylcarbamoyloxy" represents a straight or branched alkyl chain having from one to four carbon atoms attached to the nitrogen atom of a carbamoyloxy moiety. Typical N-($C_1$–$C_4$)alkylcarbamoyloxy groups include N-methylcarbamoyloxy, N-ethylcarbamoyloxy, N-propylcarbamoyloxy, N-isopropylcarbamoyloxy, N-butylcarbamoyloxy and the like.

"N,N-di-($C_1$–$C_4$)alkylcarbamoyloxy" represents two straight or branched alkyl chains having from one to four carbon atoms attached to the nitrogen atom of a carbamoyloxy moiety. Typical N,N-di-($C_1$–$C_4$)alkylcarbamoyloxy groups include N,N-dimethylcarbamoyloxy, N-methyl-N-ethylcarbamoyloxy, N-methyl-N-propylcarbamoyloxy, N-ethyl-N-isopropylcarbamoyloxy, N-propyl-N-tert-butylcarbamoyloxy and the like.

"N-($C_1$–$C_4$)alkylcarbamoylamino" represents a straight or branched alkyl chain having from one to four carbon atoms attached to the nitrogen atom of a carbamoylamino moiety. Typical N-($C_1$–$C_4$)alkylcarbamoylamino groups include N-methylcarbamoylamino, N-ethylcarbamoylamino, N-propylcarbamoylamino, N-isopropylcarbamoylamino, N-butylcarbamoylamino and the like.

"N,N-di-($C_1$–$C_4$)alkylcarbamoylamino" represents two straight or branched alkyl chains having from one to four carbon atoms attached to the nitrogen atom of a carbamoylamino moiety. Typical N,N-di-($C_1$–$C_4$)alkylcarbamoylamino groups include N,N-dimethylcarbamoylamino, N-methyl-N-ethylcarbamoylamino, N-methyl-N-propylcarbamoylamino, N-ethyl-N-isopropylcarbamoylamino, N-propyl-N-tert-butylcarbamoylamino and the like.

"Phenyl($C_1$–$C_6$)alkyl" represents a straight or branched alkyl chain having from one to six carbons with a phenyl group attached to it. Typical phenyl($C_1$–$C_6$)alkyl groups include phenylmethyl, 2-phenylethyl, 3-phenylpropyl, 1-phenylisopropyl, 4-phenylbutyl, 3-phenylisobutyl, 2-phenylsec-butyl, 5 phenylpentyl, 3-phenylhexyl, 4,4-dimethyl-4-phenylbutyl and the like.

"Phenyl($C_1$–$C_6$)alkoxy" represents a straight or branched alkoxy chain having from one to six carbon atoms with a phenyl group attached to it. Typical phenyl($C_1$–$C_6$)-alkoxy groups include phenylmethoxy, 2-phenylethoxy, 3-phenylpropoxy, 1-phenylisopropoxy, 4-phenylbutoxy, 3-phenylisobutoxy, 2-phenyl-sec-butoxy, 5-phenylpentoxy, 4-phenylhexoxy, 4,4-dimethyl-4-phenyl-butoxy and the like.

"Substituted $C_1$–$C_6$ alkyl" represents a $C_1$–$C_6$ alkyl group substituted by cyano, carboxy, halo, amino, $C_1$–$C_4$ alkoxy, $C_1$–$C_4$ alkylthio, trifluoromethyl or trifluoromethylthio. Typical substituted $C_1$–$C_6$ alkyl groups include cyanomethyl, 2-carboxyethyl, 1-chloroisopropyl, 2-ethoxybutyl, 1-aminoisopropyl, 2-ethoxybutyl, 1-methylthiopropyl, 3-trifluoromethylisobutyl, 5-trifluoromethylthiopentyl, 1,1-dimethyl-4-chlorobutyl, 6-cyanohexyl and the like.

The terms "substituted phenyl," "substituted phenoxy," "substituted phenylthio," "substituted anilino" and "substituted pyridyl" when used herein, refer to such groups substituted on the phenyl ring by one or two of the same or different groups selected from among $C_1$–$C_4$ alkyl, $C_1$–$C_4$ alkoxy, methylenedioxy, halo, hydroxy, amino, $C_1$–$C_4$ alkylamino, di-($C_1$–$C_4$)alkylamino, $C_1$–$C_4$ alkanoylamino, carboxy, carbamoyl, cyano, trifluoromethyl, and $C_1$–$C_4$ alkanoyl. Examples of such substituted groups are 4-hydroxyphenyl, 4-methylphenyl, 4-chlorophenyl, 3-chloro-4-hydroxyphenyl, 4-methoxyphenyl, 4-methylenedioxyphenyl, 3-aminophenyl, 4-chlorophenoxy, 3-ethylphenoxy, 3-hydroxyphenoxy, 2-fluorophenoxy, 4-trifluoromethylphenoxy, 2,5-dimethylphenoxy, 4-chlorophenylthio, 3,4-dichlorophenylthio, 2-methoxyphenylthio, 4-fluorophenylthio, 3 acetylaminophenylthio, 3-cyanophenylthio, 4-methylanilino, 2,4-dimethylanilino, 3-carboxyanilino, 4-methoxyanilino, 4-chloroanilino, 3-bromoanilino, 3-chloro-4-ethoxyanilino, 4-cyanoanilino, 4-carbamoylanilino and the like.

"Aryl" represents a structure selected from the group consisting of naphthyl, thienyl, furyl, benzothienyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl or thiadiazolyl.

"Arylmethyl" represents an aryl group attached to a methylene moiety. Typical arylmethyl groups include naphthylmethyl, thienylmethyl, furylmethyl, benzothienylmethyl, benzothiazolylmethyl, benzofurylmethyl and the like.

"Substituted arylmethyl" represents an arylmethyl group wherein such aryl groups are substituted by amino, hydroxy, cyano, nitro, halo, $C_1$–$C_4$ alkyl, $C_1$–$C_4$ alkoxy, phenyl, substituted phenyl or $C_1$–$C_4$ alkylsulfonylamino. Typical substituted arylmethyl groups include 2-aminonaphthylmethyl, 4-hydroxythienylmethyl, 3-cyanofurylmethyl and the like.

The term "carboxy-protecting group" represents one of the groups employed to block or protect the carboxylic acid group while reactions are carried out on other functional groups on the compound. Examples of such carboxylic acid protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxy-benzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are p-nitrobenzyl, p-methoxybenzyl and methyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The related term "protected carboxy" denotes that a carboxy group is substituted with one of the above carboxy-protecting groups.

The term "amino-protecting group" refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, benzoylmethylsulfonyl, 2-(nitro)-phenylsulfenyl, 4-phenyloxazolidin-2-one, and urethane-type blocking groups such as benzyloxycarbonyl, 4-phenylbenzyloxycarbonyl, 2-methylbenzyloxycarbonyl, 2,4-dichlorobenzyloxycarbonyl, 4-bromobenzyloxycarbonyl, 4-nitrobenzyloxycarbonyl, 1,1-diphenyleth-1-yloxycarbonyl, 2-phenylprop-2-yloxycarbonyl, cyclopentyloxycarbonyl, 1-methylcyclopentyloxycarbonyl, cyclohexyloxycarbonyl, 1-methylcyclohexyloxycarbonyl, 2-(4-toluylsulfonyl)ethoxycarbonyl, 2-(methylsulfonyl)ethoxycarbonyl, 2 (tri-phenylphosphino)ethoxycarbonyl, 9-fluorenylmethoxycarbonyl ("FMOC"), allyloxycarbonyl, 1-(trimethylsilylmethyl)-prop-1-enyloxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)-benzyloxycarbonyl, isobornyloxycarbonyl, 1-piperidyloxycarbonyl and the like. Preferred amino-protecting groups are benzyloxycarbonyl and 4-phenyloxazolidin-2-one. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" denotes that an amino is substituted with an amino-protecting group discussed above.

The term "pharmaceutically acceptable salt" refers to salts of the compounds of formulae I and III which are substantially non-toxic to living organisms. The cephalosporin, carbacephalosporin, penicillin and azetidin-2-one compounds form salts with suitable bases, in particular, the pharmaceutically acceptable, non-toxic salts. The carboxy group can form salts with the alkali and alkaline earth metal hydroxides, carbonates and bicarbonates. Examples of such pharmaceutically acceptable salts are the sodium, potassium, calcium, and magnesium salts. Salts can also be formed with amines such as dibenzylamine, cyclohexylamine, triethylamine, ethanolamine, diethanolamine and like amines. Likewise, when the compounds are substituted by two or more carboxy groups, di- and tri-salts are obtained by conventional salt-forming methods. In addition, the cephalosporin, carbacephalosporin, penicillin and azetidin-2-one compounds can form salts with suitable acids to provide pharmaceutically acceptable salts. Typical examples of suitable acids include hydrochloric, hydrobromic, sulfuric, phosphoric, oxalic, carbonic, citric acid and the like.

The term "non-basic solvent" represents any organic solvent that does not contain a free amino group. Typical non-basic solvents include methylene chloride, ethyl acetate, tetrahydrofuran, ethylene glycol dimethyl ether, dioxane, diethyl ether, carbon disulfide, chloroform, hexane, carbon tetrachloride, cyclohexane and the like.

The term "residue of a carboxylic acid" represented by R of —C(O)—R in formula I includes those 7-position side chains known in the cephalosporin and carbocephalosporin arts, and those 6-position side chains known in the penicillin art. These side chains are residues of $C_1$–$C_{20}$ carboxylic acids, and are exemplified when R is hydrogen, $C_1$–$C_6$ alkyl, substituted $C_1$–$C_6$ alkyl, naphthyl, phenyl, substituted phenyl, arylmethyl, substituted arylmethyl, or a group of the formula

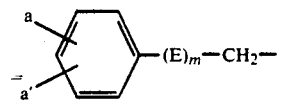

where a and a' independently are hydrogen, halo, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, carboxy, carbamoyl, aminosulfonyl, hydroxymethyl, aminomethyl or carboxymethyl; E is —O— or —S—; and m is 0 or 1, or R is a group of the formula

where $R^0$ is cyclohex-1,4-dienyl, phenyl, substituted phenyl or aryl and Q is hydroxy, $C_1$–$C_4$ alkanoyloxy, carboxy, sulfo, amino, sulfoamino or a structure selected from the group consisting of

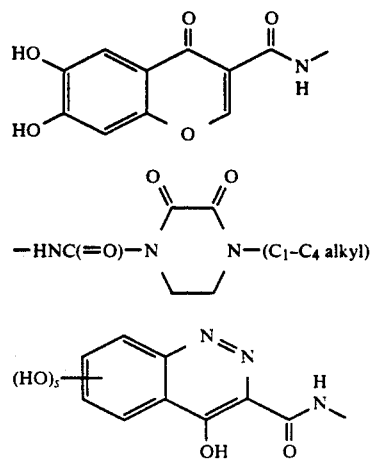

-continued

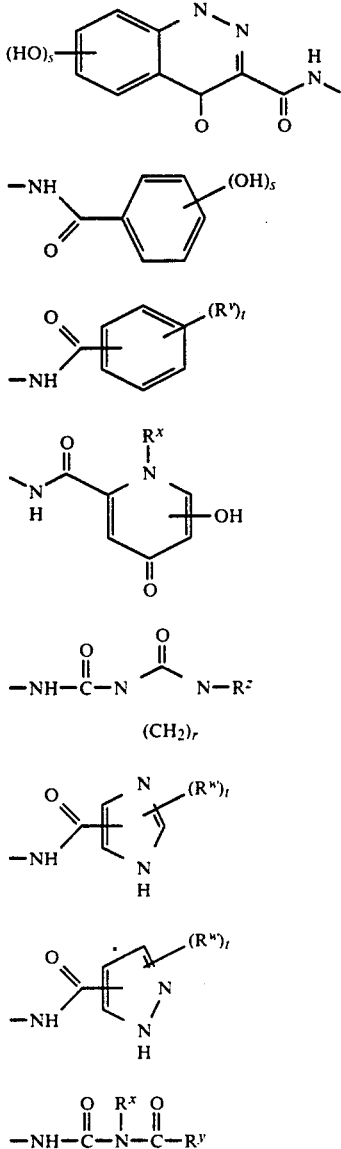

where
 $R^x$ is hydrogen or $C_1$-$C_3$ alkyl;
 $R^z$ is hydrogen, $C_1$-$C_3$ alkylsulfonyl, $C_1$-$C_3$ alkyl or $C_1$-$C_4$ alkanoyl;
 $R^y$ is $C_1$-$C_4$ alkyl, furyl, thienyl, phenyl, halophenyl, nitrophenyl, styryl, halostyryl, nitrostyryl or a group of the formula —$NR^xR^z$, where $R^x$ and $R^z$ are defined as above;
 $R^v$ is $C_1$-$C_4$ alkyl, carboxy, hydroxy or halo;
 $R^w$ is $C_1$-$C_4$ alkyl, carboxy, amino or halo;
 r is 2 or 3; s is 1, 2, or 3; and t is 0 or 1; or R is a group of the formula

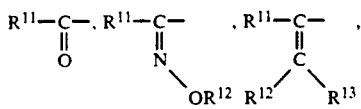

where $R^{11}$ is cyclohex-1,4-dienyl, phenyl, substituted phenyl or aryl;
$R^{13}$ is hydrogen or halo;
$R^{12}$ is hydrogen, $C_1$-$C_4$ alkyl, $C_2$-$C_4$ alkenyl, arylmethyl, a cyclic lactam group of the formula

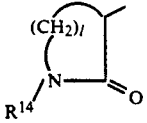

where l is 2, 3 or 4 and $R^{14}$ is hydrogen or $C_1$-$C_3$ alkyl, or $R^{12}$ is a carboxy-substituted alkyl or a cycloalkyl group of the formula

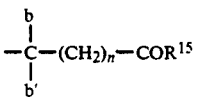

where b and b' independently are hydrogen or $C_1$-$C_3$ alkyl, n is 0, 1, 2 or 3; and b and b', when taken together with the carbon to which they are bonded, form a 3- to 6-membered carbocyclic ring; and $R^{15}$ is hydroxy, $C_1$-$C_4$ alkylamino or di($C_1$-$C_4$)alkylamino.

While all combinations of the variables listed in the above formulae provide compounds amenable to the process of the present invention, certain of the above compounds are preferred for such process. For example, preferred compounds of the formula II are those compounds wherein $R^1$, $R^2$, and $W^1$ are as defined above; f is 1; $R^9$ and $R^{10}$ are combined to form a double bond; Z is —S— or —$CH_2$—; and A is hydrogen, halo, cyano, hydroxy, azido, $C_1$-$C_6$ alkyl, halo($C_1$-$C_6$)alkyl, cyano($C_1$-$C_6$)alkyl, C-$C_6$ alkylthio, $C_1$-$C_6$ alkoxy, or trifluoromethanesulfonyloxy. Of these preferred compounds, especially preferred are those compounds wherein A is halo, halo($C_1$-$C_6$)alkyl, trifluoromethanesulfonyloxy, or $C_1$-$C_6$ alkyl.

In addition, preferred compounds of the formula II are those compounds wherein $R^1$, $R^2$, and $W^1$ are as defined above; f is 0, Z is —S—, —S(O)— or —$SO_2$—; A is methyl; $R^9$ is methyl and $R^{10}$ is hydrogen.

The compounds of formulae II and IV can be prepared using chemical synthetic methods well-known to persons skilled in the art. The ester cleavage process involves reacting an appropriately substituted cephalosporin or 1-carbacephalosporin compound that has an ester at the four-position, a penicillin compound that has an ester at the three-position or an azetidin-2-one compound that has an ester at the 1 position, with lithium iodide in a suitable solvent.

The above reaction is carried out by simply combining an appropriately substituted cephalosporin, 1-carbacephalosporin, penicillin or azetidin-2-one ester compound with lithium iodide in a non-basic solvent that has a dielectric constant of between about zero and about fifteen. The lithium iodide is generally employed in an amount ranging from equimolar proportions to about a six molar excess of the lithium iodide. The lithium iodide is preferably employed in at least about a two molar excess relative to the cephalosporin, 1-carbacephalosporin, penicillin or azetidin-2-one compound.

Suitable solvents for this process include any organic solvent which is non-basic, that is, does not contain a free amino group, and has a dielectric constant between about 0 and about 15. The reaction is preferably conducted in a solvent with a dielectric constant of between about 0 and 10. Especially preferred solvents include ethyl acetate and tetrahydrofuran.

The reaction is substantially complete within 72 hours when conducted at a temperature in the range of from about 20° C. to the reflux temperature of the reaction mixture. The reaction is preferably conducted in the range of from about 55° C. to about 80° C. for about 1 to 16 hours, such mild conditions being especially suitable for β-lactams.

Once the reaction is complete, the product may be isolated as the lithium salt or converted to the carboxylic acid form by dissolving the product in a suitable solvent and acidifying the resultant solution to a pH from about 1.8 to about 3.5. The product may be isolated, in either form, by procedures well-known in the art. For example, the precipitated solid may be collected by filtration or the reaction solvent may be removed by extraction, evaporation or decantation. The product may be further purified, if desired, by common techniques such as crystallization or chromatography over solid supports such as silica gel or alumina.

The following Examples further illustrate specific aspects of the present invention. It is to be understood, however, that the examples are included for illustrative purposes only, are not intended to limit the scope of the invention in any respect, and should not be so construed.

EXAMPLE 1

7β-[(S)-4-phenyloxazolidin-2-one-3-yl ]-1-carba(1-dethia)-3-trifluoromethanesulfonyloxy-3-cephem-4-carboxylic acid To a slurry of 3.06 g (5 mmol) of p-nitrobenzyl 7β-[(S)-4-phenyloxazolidin-2-one-3-yl ]-1-carba(1-dethia)-3-trifluoromethanesulfonyloxy-3-cephem-4-carboxylate and 30 ml of ethyl acetate, was added 2.0 g (15 mmol) of lithium iodide. The resulting reaction mixture was allowed to react at room temperature for approximately three days. When the reaction was complete, as determined by high performance liquid chromatography, 50 ml of water was added which caused the precipitation of lithium 7β-[(S)-4-phenyloxazolidin-2-one-3-yl ]-1-carba(1-dethia)-3-trifluoromethylsulfonyloxy-3-cephem-4-carboxylate. The resulting mixture was stirred to redissolve this salt and then the resulting layers were separated and the aqueous layer was acidified to a pH of 1.89 with concentrated hydrochloric acid, resulting in the formation of a light yellow solid. This solid was isolated by filtration and washed sequentially with water and diethyl ether to provide 1.19 g of the desired titled product.

Analysis for $C_{18}H_{15}N_2SO_8F_3$: Calc.: C, 45.38: H, 3.17: N, 5.88: Found: C, 45.65; H, 3.31; N, 6.05.

NMR(DMSO, d-6): δ 1.95 (m, 1); 2.03 (m, 1); 2.55 (m, 2); 3.78 (m, 1); 4.03 (dd, 1); 4.52 (d, 1); 4.70 (t, 1); 5.02 (dd, 1); 7.40 (m, 5).

EXAMPLE 2

7β-[(S)-4-phenyloxazolidin-2-one-3-yl]-1-carba(1-dethia)-3-trifluoromethanesulfonyloxy-3-cephem-4-carboxylic acid The titled compound was prepared substantially in accordance with the method detailed in Example 1, except that the reaction mixture was allowed to react for about 90 minutes at 65° C. to provide 1.73 g of a yellow solid.

NMR(DMSO, d-6): δ 1.95 (m, 1); 2.08 (m, 1); 2.58 (m, 2); 3.80 (m, 1); 4.10 (dd, 1); 4.55 (d, 1); 4.70 (t, 1); 5.03 (dd, 1); 7.30 (m, 5).

EXAMPLE 3

7β-[(S)-4-phenyloxazolidin-2-one-3-yl]-1-carba(1-dethia)-3-chloro-3-cephem-4-carboxylic acid To a slurry of 0.996 g (2 mmol) of p-nitrobenzyl 7β-[(S)-4-phenyloxazolidin-2-one-3-yl]-1-carba(1-dethia)-3-chloro-3-cephem-4-carboxylate and 10 ml of ethylene glycol dimethyl ether, was added 0.80 g (6 mmol) of lithium iodide. The resulting reaction mixture was then heated to reflux and allowed to react for about 3 hours. When the reaction was complete, as determined by high performance liquid chromatography, the solution was cooled to room temperature and 10 ml of water was added which caused the precipitation of lithium 7β-[(S)-4-phenyloxazolidin-2-one-3-yl]-1-carba(1-dethia)-3-chloro-3-cephem-4-carboxylate. This precipitate was redissolved by the addition of 10 mol of methylene chloride. The resulting layers were separated and the aqueous layer was acidified to a pH of 1.94 with 1N hydrochloric acid, resulting in the formation of a light yellow solid. This solid was isolated by filtration and washed with diethyl ether to provide 0.41 g of the desired titled product.

Analysis for $C_{17}H_{15}N_2O_5Cl$: Calc.: C, 56.29; H, 4.17; N, 7.72; Cl, 9.77; Found: C, 56.23; H, 4.30; N, 7.60; Cl, 10.08.

NMR(DMSO, d-6): δ 1.95 (m, 2); 2.55 (m, 2); 3.72 (m, 1); 4.08 (dd, 1); 4.42 (d, 1); 4.70 (t, 1); 5.00 (dd, 1); 7.40 (m, 5).

EXAMPLE 4 lithium 7β-[(S)-4-phenyloxazolidin-2-one-3-yl]-1-carba(1-dethia)-3-chloro-3-cephem-4-carboxylate To a solution of 6 g (12.1 mmol) of p-nitrobenzyl 7β-[(S)-4-phenyloxazolidin-2-one-3-yl]-1-carba(1-dethia)-3-chloro-3-cephem-4-carboxylate in 73.5 ml of tetrahydrofuran, was added 9.72 g (72.6 mmol) of lithium iodide. The resulting reaction mixture was then heated to reflux and allowed to react for about 4½ hours. When the reaction was complete, as determined by high performance liquid chromatography, the solution was cooled, resulting in the formation of a white solid. This solid was isolated by filtration and washed sequentially with cold tetrahydrofuran and then diethyl ether to provide 3.83 g of the desired titled product.

NMR(DMSO, d-6/TFA): δ 1.98 (m, 2); 2.52 (m, 2); 3.73 (m, 1); 4.08 (dd, 1); 4.42 (d, 1); 4.70 (t, 1); 5.00 (dd, 1); 7.38 (m, 5).

EXAMPLE 5 lithium 7β-[(S)-4-phenyloxazolidin-2-one-3-yl]-1-carba(1-dethia)-3-chloro-3-cephem-4-carboxylate The titled compound was prepared substantially in accordance with the method detailed in Example 4 using 0.996 g (2 mmol) of p-nitrobenzyl 7β-[(S)-4-phenyloxazolidin-2-one-3-yl]-1-carba(1-dethia)-3-chloro-3-cephem-4-carboxylate, 10 ml of methylene chloride and 1.6 g (12 mmol) of lithium iodide. The reaction mixture was allowed to react for approximately 5 days at reflux temperature to provide 1.72 g of a yellow solid, of which 40% was the desired titled product.

EXAMPLE 6 lithium 7β-[(S)-4-phenyloxazolidin-2-one-3-yl]-1-carba(1-dethia)-3-bromo-3-cephem-4-carboxylate The titled compound was prepared substantially in accordance with the method detailed in Example 4 using 0.542 g (1 mmol) of p-nitrobenzyl 7β-[(S)-4-phenyloxazolidin-2-one-3-yl]-1-carba(1-dethia)-3-bromo-3-cephem-4-carboxylate, 6.1 ml of tetrahydrofuran and 0.803 g (6 mmol) of lithium iodide. The reaction mixture was allowed to react for about 2¼ hours at reflux to provide 0.29 g of a white solid.

Analysis for $C_{17}H_{14}N_2O_5Br^-Li^+$ Calc.: C, 49.42; H, 3.42; N, 6.78; 0, 19.36; Br, 19.34; Found: C, 49.39; H, 3.41; N, 6.53; 0, 19.57; Br, 19.37.

NMR(DMSO, d-6/TFA): δ 1.95 (m, 2); 2.68 (m, 2); 3.75 (m, 1); 4.10 (dd, 1); 4.45 (d, 1); 4.70 (t, 1); 4.98 (dd, 1); 7.35 (m, 5).

EXAMPLE 7

7β-[(S)-4-phenyloxazolidin-2-one-3-yl]-1-carba(1-dethia)-3-chloro-3-cephem-4-carboxylic acid The titled compound was prepared substantially in accordance with the method detailed in Example 1 using 1.50 g (4 mmol) of methyl 7β-[(S)-4-phenyloxazolidin-2-one-3-yl]-1-carba(1-dethia)-3-chloro-3-cephem-4-carboxylate, 16 ml of ethyl acetate and 1.61 g (12 mmol) of lithium iodide. The reaction mixture was allowed to react for about 4½ hours at reflux temperature to provide 0.65 g of a yellow solid.

Analysis for $C_{17}H_{15}N_2O_5Cl$: Calc.: C, 56.29; H, 4.17; N, 7.72; Found: C, 56.32; H, 4.46; N, 7.58.

NMR(DMSO, d-6): δ 1.95 (m, 2); 2.58 (m, 2); 3.78 (m, 1); 4.10 (dd, 1); 4.45 (d, 1); 4.76 (t, 1); 5.00 (dd, 1); 7.40 (m, 5).

EXAMPLE 8 lithium 7β-[(S)-4-phenyloxazolidin-2-one-3-yl]-1-carba(1-dethia)-3-chloro-3-cephem-4-carboxylate The titled product was prepared substantially in accordance with the method detailed in Example 4 using 0.377 g (1 mmol) of methyl 7β-[(S)-4-phenyloxazolidin-2-one-3-yl]-1-carba(1-dethia)-3-chloro-3-cephem-4-carboxylate, 6.1 ml of tetrahydrofuran and 0.803 g (6 mmol) of lithium iodide. The reaction mixture was allowed to react for about 8 hours at reflux temperature to provide 0.20 g of a white solid.

NMR(DMSO,d-6/D₂O): δ 1.91 (m, 2); 2.32 (m, 2); 3.52 (m, 1); 4.06 (dd, 1); 4.22 (d, 1); 4.68 (t, 1); 4.95 (dd, 1); 7.38 (m, 5).

EXAMPLE 9 lithium 7β-N-benzyloxycarbonyl-1-carba(1-dethia)-3-chloro-3-cephem-4-carboxylate The titled product was prepared substantially in accordance with the method detailed in Example 4 using 0.24 g (0.5 mmol) of p-nitrobenzyl 7β-N-benzyloxycarbonyl-1-carba(1-dethia)-3-chloro-3-cephem-4-carboxylate, 5 ml of ethyl acetate and 0.2 g (1.5 mmol) of lithium iodide. The reaction mixture was allowed to react for about 3 hours at reflux temperature to provide 0.16 g of a light yellow solid, of which 85% was the desired titled compound.

NMR(DMSO, d-6/TFA): δ 1.80 (m, 2); 2.52 (m, 2); 3.82 (m, 1); 5.02 (q, 2); 5.18 (m, 1); 7.30 (m, 5); 8.12 (d, 1).

EXAMPLE 10 lithium 7β-N-benzyloxycarbonyl-1-carba(1-dethia)-3-chloro-3-cephem-4-carboxylate The titled product was prepared substantially in accordance with the method detailed in Example 4 using 0.24 g (0.5 mmol) of p-methoxybenzyl 7β-N-benzyloxycarbonyl-1-carba(1-dethia)-3-chloro-3-cephem-4-carboxylate, 5 ml of ethyl acetate and 0.2 g (1.5 mmol) of lithium iodide. The reaction mixture was allowed to react for about 4 hours at reflux temperature to provide 0.10 g of a white solid.

Analysis for $C_{16}H_{14}N_2O_5Cl^-Li^+$ Calc.: C, 53.88; H, 3.96; N, 7.85; 0, 22.43; Cl, 9.94; Found: C, 53.88; H, 4.15; N, 7.60; 0, 22.63; Cl, 9.68.

NMR(DMSO, d-6/TFA): δ 1.78 (m, 2); 2.57 (m, 2); 3.82 (m, 1); 5.02 (q, 2); 5.18 (m, 1); 7.30 (m, 5); 8.12 (d, 1).

EXAMPLE 11

3-[(S)-4-phenyloxazolidin-2-one-3-yl]-4-[2-furylethyl]-azetidin-2-one-1-ethanoic acid The titled compound was prepared substantially in accordance with the method detailed in Example 1 using 2.60 g (5 mmol) of p-nitrobenzyl-3-[(S)-4-phenyloxazolidin-2-one-3-yl]-4-[2-furylethyl]-azetidin-2-one-1-ethanoate, 20 ml of ethyl acetate and 2.0 g (15 mmol) of lithium iodide. The reaction mixture was allowed to react for approximately 7½ hours at reflux temperature to provide 1.54 g of a light yellow solid.

Analysis for $C_{20}H_{20}N_2O_6$: Calc.: C, 62.49; H, 5.24; N, 7.29; Found: C, 62.46; H, 5.27; N, 7.22.

NMR(CDCl₃): δ 1.58 (m, 1); 1.68 (m, 1); 2.56 (t, 2); 3.34 (d, 1); 3.85 (q, 1); 4.20 (d, 1); 4.22 (t, 1); 4.55 (d, 1); 4.65 (t, 1); 4.88 (m, 1); 7.32 (m, 5).

EXAMPLE 12

7β-amino-3-chloro-3-cephem-4-carboxylic acid

To a slurry of 3.7 g (10 mmol) of p-nitrobenzyl 7β-amino-3-chloro-3-cephem-4-carboxylate and 61 ml of tetrahydrofuran, was added 8.03 g (60 mmol) of lithium iodide. The resulting reaction mixture was then heated to reflux and allowed to react for about 2½ hours. The solution was cooled to complete the precipitation of lithium 7β-amino-3-chloro-3-cephem-4-carboxylate. This precipitate was isolated by filtration, slurried in 25 ml of tetrahydrofuran and then acidified to a pH of 3.7 with 1N hydrochloric acid resulting in the formation of a light solid. This solid was isolated by filtration and washed with a 25:3 tetrahydrofuran/water solution to provide 0.59 g of the desired titled product.

NMR(DMSO, d-6/TFA): δ 3.72 (d, 1); 4.00 (d, 1); 5.18 (d, 1); 5.28 (d, 1).

EXAMPLE 13 lithium 7β-amino-1-carba(1-dethia)-3-chloro-3-cephem-4-carboxylic acid

The titled product was prepared substantially in accordance with the method detailed in Example 4 using 1.94 g (5 mmol) of p-nitrobenzyl 7β-amino-1-carba(1-dethia)-3-chloro-3-cephem-4-carboxylate monohydrochloride, 19 ml of ethyl acetate and 1.34 g (10 mmol) of lithium iodide. The reaction mixture was allowed to react for approximately 24 hours at reflux temperature to provide 1.57 g of a light green solid of which 35% was desired titled product.

EXAMPLE 14

7β-amino-3-chloro-3-cephem-4-carboxylic acid

To a slurry of 4.06 g (10 mmol) of p-nitrobenzyl 7β-amino 3-chloro-3-cephem-4-carboxylate monohydrochloride and 40 ml of ethyl acetate, was added 4.01 g (30 mmol) of lithium iodide. The resulting reaction mixture was heated to reflux and allowed to react for about 3 hours. When the reaction was complete, as determined by high performance liquid chromatography, the mixture was cooled to room temperature and 40 ml of water was added and then the solution was basified to pH 7.3 with 5% sodium bicarbonate solution. The resulting layers were separated and 10 ml of methylene chloride was added to the aqueous layer which caused an emulsion which slowly separated. The aqueous layer was isolated and then slowly acidified to pH 3.2 with concentrated hydrochloric acid resulting in the formation of a light tan solid. This solid was isolated by filtration and washed sequentially with acetone and diethyl ether to provide 1.2 g of a solid, of which 73% was the desired titled product.

EXAMPLE 15 lithium 7β-N-[3-phenyl-1-methylpropen-3-one-1-yl]-3-chloro 3 cephem-4-carboxylate The titled product was prepared substantially in accordance with the method detailed in Example 4 using 1.03 g (2 mmol) of p-nitrobenzyl 7β-N-[3-phenyl-1-methyl-propen-one-1-yl]-3-chloro-3-cephem-4-carboxylate, 12 ml of tetrahydrofuran and 0.81 g (6 mmol) of lithium iodide. The reaction mixture was allowed to react for about 12 hours at reflux temperature to provide 0.54 g of a light tan solid.

NMR(DMSO, d-6): δ 2.10 (s, 3); 3.40 (d, 1); 3.80 (d, 1); 5.12 (d, 1); 5.63 (m, 1); 5.95 (s, 1); 7.43 (m, 2); 7.85 (d, 2); 11.40 (d, 1).

EXAMPLE 16 lithium 7β-N-methoxycarbonyl-3-chloro-3-cephem-4-carboxylate

The titled product was prepared substantially in accordance with the method detailed in Example 4 using 2.14 g (5 mmol) of p-nitrobenzyl 7β-N-methoxycarbonyl-3-chloro-3-cephem-4-carboxylate, 20 ml of ethyl acetate and 2.0 g (15 mmol) of lithium iodide. The reaction mixture was allowed to react for about 90 minutes at reflux temperature to provide 1.39 g of a dark brown solid, of which 94% was the desired titled product.

NMR(DMSO, d-6): δ 3.30 (d, 1); 3.52 (s, 3); 3.72 (d, 1); 4.95 (d, 1); 5.28 (m, 1); 8.28 (d, 1).

EXAMPLE 17 lithium 7β-[(S)-4-phenyloxazolidin-2-one-3-yl]-1-carba(1-dethia)-3-iodo-3-cephem-4-carboxylate To a slurry of 2.95 g (5 mmol) of p-nitrobenzyl 7β-[(S)-4-phenyloxazolidin-2-one-3-yl]-1-carba(1-dethia)-3-iodo-3-cephem-4-carboxylate and 30.5 of tetrahydrofuran, was added 4.0 g (30 mmol) of lithium iodide. The resulting reaction mixture was then heated to reflux and allowed to react for about 7½ hours. When the reaction was complete, as indicated by high performance liquid chromatography, 30 ml of ethyl acetate was added slowly to the reaction mixture. The mixture was then cooled to room temperature resulting in the formation of a white solid. This solid was isolated by filtration and washed sequentially with a 1:1 tetrahydrofuran/ethyl acetate solution, ethyl acetate and diethyl ether to provide 1.49 g of the desired titled product.

Analysis for $C_{17}H_{14}N_2O_5I^-Li^+$ Calc.: C, 44.37; H, 3.07; N, 6.09; I, 27.58; Found: C, 44.10; H, 3.04; N, 5.80; I, 27.38.

NMR(DMSO, d-6/TFA): δ 1.88 (m, 2); 2.68 (m, 2); 3.75 (m, 1); 4.08 (q, 1); 4.43 (d, 1); 4.68 (t, 1); 4.98 (q, 1); 7.35 (m, 5).

EXAMPLE 18

7β-[(S)-4-phenyloxazolidin-2-one-3-yl]-1-carba(1-dethia)-3-trifluoromethyl-3-cephem-4-carboxylic acid To a slurry of 5.31 g (10 mmol) of p-nitrobenzyl 7β-[(S)-4-phenyloxazolidin-2-one-3-yl]-1-carba(1-dethia)-3-trifluoromethyl-3-cephem-4-carboxylate and 106 ml of ethyl acetate, was added 2.00 g (15 mmol) of lithium iodide. The resulting reaction mixture was then heated to reflux and allowed to react for about 7 hours resulting in the precipitation of lithium 7β-[(S)-4-phenyloxazolidin-2-one-3-yl]-1-carba(1-dethia)-3-trifluoromethyl-3-cephem-4-carboxylate. The reaction mixture was then cooled to room temperature and allowed to react for another 12 hours. When the reaction was complete, as indicated by high performance liquid chromatography, 100 ml of water was added to dissolve the lithium salt. The resulting layers were separated and the aqueous layer was acidified to pH 1.87 with concentrated hydrochloric acid, resulting in the formation of a light yellow solid. This solid was isolated by filtration and washed with water to provide 3.38 g of the desired titled product.

Analysis for $C_{18}H_{15}N_2O_5F_3$: Calc.: C, 54.55; H, 3.82; N, 7.07; F, 14.38; Found: C, 54.78; H, 3.97; N, 6.87; F, 14.45.

NMR(DMSO, d-6): δ 1.67 (m, 2); 2.07 (m, 1); 2.28 (m, 1); 3.78 (m, 1); 4.14 (dd, 1); 4.57 (d, 1); 4.73 (t, 1); 5.03 (dd, 1); 7.38 (m, 5); 14.03 (s, 1).

EXAMPLE 19 lithium 7β-[(S)-4-phenyloxazolidin-2-one-3-yl]-1-carba(1-dethia)-3-trifluoromethyl-3-cephem-4-carboxylate The titled product was prepared substantially in accordance with the method described in Example 4 using 1.06 g (2 mmol) of p-nitrobenzyl 7β-[(S)-4-phenyloxazolidin-2-one-3-yl]-1-carba(1-dethia)-3-trifluoromethyl-3-cephem-4-carboxylate, 12.2 ml of dioxane and 1.61 g (12 mmol) of lithium iodide. The reaction mixture was allowed to react overnight at 65° C. to provide 1.24 g of a dark yellow solid which was a mixture of the desired titled product and lithium iodide.

EXAMPLE 20

6-phthalimido penicillanic acid-1β-oxide

The titled compound was prepared substantially in accordance with the method detailed in Example 1 using 1.25 g (2.5 mmol) of p-nitrobenzyl-6-phthalimido penicillinate-1β-oxide, 20 ml of ethyl acetate and 1.0 g (7.5 mmol) of lithium iodide. The reaction mixture was allowed to react for approximately 2 hours at reflux temperature to provide 0.54 g of a white solid.

NMR(DMSO d6): δ 1.20 (s, 3); 1.60 (s, 3); 4.35 (s, 1); 4.80 (d, 1); 6.00 (d, 1); 7.85 (m, 4); 13.70 (bs, 1)

We claim:

1. A process for producing a compound of the formula I

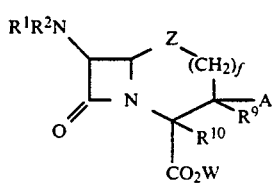

or a pharmaceutically acceptable salt thereof; which comprises reacting, in a non-basic solvent having a dielectric constant between about 0 and about 15, lithium iodide and a compound of the formula II or a salt of a compound of the formula II that is capable of forming a salt,

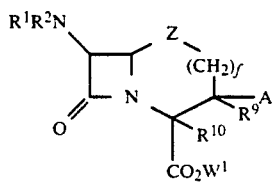

wherein:

W is lithium ion;

$W^1$ is a carboxy-protecting group;

Z is —S—, —S(O)—, —SO$_2$— or —CH$_2$—;

$R^9$ is hydrogen, $C_1$-$C_6$ alkyl or is combined with $R^{10}$ to form a double bond;

$R^{10}$ is hydrogen or is combined with $R^9$ to form a double bond;

f is 0 or 1, with the provisos that when f is 1, $R^9$ and $R^{10}$ combine to form a double bond and when f is 0, A is $C_1$-$C_6$ alkyl;

$R^1$ and $R^2$ are independently hydrogen, $C_1$-$C_6$ alkyl, amino-protecting group or —C(O)—R where R is the residue of a carboxylic acid, with the proviso that when one of $R^1$ or $R^2$ is —C(O)—R then the other cannot be hydrogen;

A is hydrogen or a substituent selected from those found in the cephalosporin, 1-carbacephalosporin or penicillin arts.

2. A process of claim 1 for producing a compound of formula I wherein f is 1 and A is hydrogen, halo, cyano, hydroxy, azido, $C_1$-$C_6$ alkyl, halo($C_1$-$C_6$)alkyl, cyano($C_1$-$C_6$)alkyl, $C_1$-$C_6$ alkylthio, $C_1$-$C_6$ alkoxy, trifluoromethanesulfonyloxy or a group of the formula —C(O)—$R^3$, where $R^3$ is hydroxy, halo, azido, $C_1$-$C_6$ alkoxy, 2-[tri($C_1$-$C_4$)alkylsilyl]ethoxy, $C_2$-$C_6$ alkenyloxy, $C_2$-$C_6$ alkynyloxy, $C_1$-$C_4$ alkoxycarbonyloxy, phenoxy, or substituted phenoxy;

or $R^3$ is $C_1$-$C_6$ alkoxy substituted by one or two of the same or different groups selected from among hydroxy, amino, $C_1$-$C_4$ alkylamino, di($C_1$-$C_4$)alkylamino, $C_1$-$C_4$ alkanoylamino, halo, $C_1$-$C_4$ alkoxy, $C_1$-$C_4$ alkylthio, cyano, carboxy, $C_1$-$C_4$ alkoxycarbonyl, carbamoyl, carbamoyloxy, N-($C_1$-$C_4$)alkylcarbamoyloxy, N,N-di($C_1$-$C_4$)alkylcarbamoyloxy, $C_1$-$C_4$ alkoxycarbonyloxy, phenoxycarbonyloxy, $C_1$-$C_4$ alkoxycarbonylamino, phenoxycarbonylamino, N-($C_1$-$C_4$)alkylcarbamoylamino, N,N-di($C_1$-$C_4$)alkylcarbamoylamino, N-phenylcarbamoylamino, anilino, substituted anilino, phenyl, substituted phenyl or a heterocyclic amino group of the formula —NHR$^4$, where $R^4$ is thienyl, furyl or a 5-membered nitrogen-containing heterocyclic ring represented by the formulae

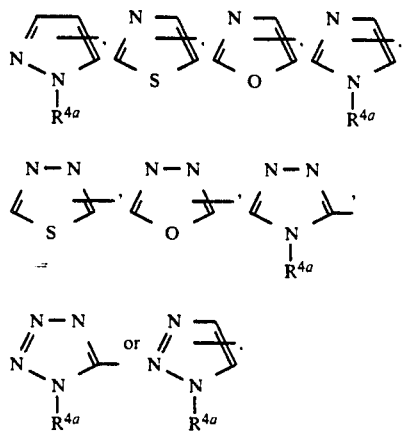

where $R^{4a}$ is hydrogen, $C_1$-$C_4$ alkyl or $C_1$-$C_4$ alkyl substituted by carboxy, sulfo or di($C_1$-$C_4$)alkylamino, or $R^4$ is a 6-membered nitrogen-containing ring represented by the formulae

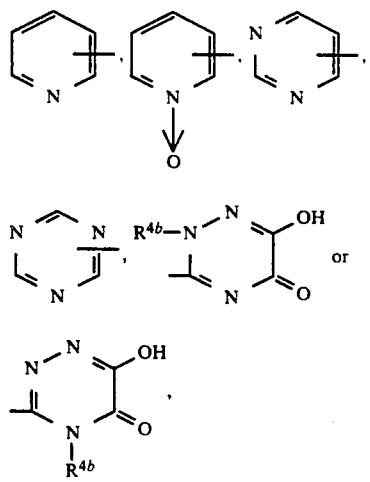

where $R^{4b}$ is hydrogen or $C_1$-$C_4$ alkyl, or a heterocyclic thio group of the formula —SR$^5$, where $R^5$ is phenyl, substituted phenyl or $R^4$ as defined above;

or a quaternary heterocyclic group of the formula X⊖R⁶⊕—. where R⁶⊕ is a nitrogen-containing heterocyclic represented by the formulae

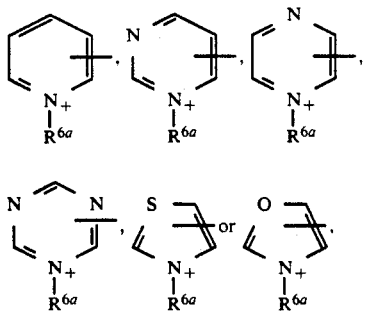

where R⁶ᵃ is $C_1$-$C_4$ alkyl, benzyl or $CH_2COCH_3$; and X⊖ is a halide, sulfate or nitrate anion;

or a heterocyclic group of the formula X⊖R⁶⊕—S—, where R⁶⊕ and X⊖ are as defined above;

or a heterocyclic group R⁴ as defined above;

or R³ is an amino group represented by the formula —NR³ᵃR³ᵇ, where R³ᵃ and R³ᵇ are independently hydrogen, phenyl, substituted phenyl, $C_1$-$C_4$ alkyl, or $C_1$-$C_4$ alkyl substituted by one or two of the same or different groups selected from among halo, hydroxy, $C_1$-$C_4$ alkanoyloxy, $C_1$-$C_4$ alkylsulfonyloxy, phenyl, substituted phenyl, amino, or $C_1$-$C_4$ alkanoylamino;

or R³ᵃ and R³ᵇ can be taken together with the nitrogen atom to which they are bonded to form a 5-7 membered ring represented by the formula

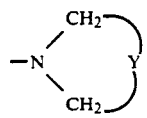

where Y is $(-CH_2-)_p$ or $-CH_2-Y^1-CH_2-$ where p is 2, 3 or 4 and $Y^1$ is —O—, —S— or —N(R³ᶜ)— where R³ᶜ is hydrogen or $C_1$-$C_4$ alkyl;

or R³ᵃ is hydrogen and R³ᵇ is $C_1$-$C_4$ alkyl substituted by a heterocyclic R⁴, a heterocyclic amino group —NHR⁴, a heterocyclic thio group —SR⁴ or a quaternary heterocyclic group X⊖R⁶⊖—, where R⁴, R⁶⊕ and X⊖ are as defined above;

or R³ is phenyl, substituted phenyl or a heterocyclic amino group —NHR⁴, where R⁴ is as defined above;

or R³ is $C_1$-$C_4$ alkyl or $C_1$-$C_4$ alkyl substituted by hydroxy, $C_1$-$C_4$ alkanoyloxy, $C_1$-$C_4$ alkoxy, $C_1$-$C_4$ alkylthio, halo, carboxy, cyano, amino, $C_1$-$C_4$ alkylamino, di($C_1$-$C_4$)alkylamino, $C_1$-$C_4$ alkanoylamino, $C_1$-$C_4$ alkylsulfonylamino, $C_1$-$C_4$ alkylsulfonyloxy, phenyl, substituted phenyl, phenylthio, substituted phenylthio, phenoxy, substituted phenoxy, anilino, substituted anilino, a heterocyclic group R⁴, a heterocyclic amino group —NHR⁴, a heterocyclic thio group —SR⁴ or a quaternary heterocyclic group X⊖R⁶⊖— or X⊕R⁶⊖—S—, where R⁴, R⁶⊕, and X⊖ are as defined above;

or R³ is phenyl, thienyl, furyl, pyridyl, pyrimidyl, imidazolyl, pyrazolyl, tetrazolyl, oxazolyl, thiazolyl, thiadiazolyl or oxadiazolyl or said phenyl or heterocycle substituted by one or two of the same or different substituents selected from $C_1$-$C_4$ alkyl, $C_1$-$C_4$ alkoxy, halo, amino or hydroxy;

or R³ is a carboxy group or a derivative of a carboxy group represented by the formula —C(O)R⁷ where R⁷ is hydrogen, hydroxy, $C_1$-$C_4$ alkoxy, phenoxy, substituted phenoxy, tri($C_1$-$C_4$)alkylsilyloxy, amino, $C_1$-$C_4$ alkylamino, di($C_1$-$C_4$)alkylamino, phenyl, substituted phenyl or $C_1$-$C_4$ alkyl;

or R³ is a group of the formula X⊖R⁸⊕—CH₂ where X⊖ is as defined above and ⊕R⁸ is pyridinium or pyridinium substituted by one or two of the same or different groups selected from among $C_1$-$C_4$ alkyl, $C_1$-$C_4$ alkoxy, $C_1$-$C_4$ alkylthio, hydroxy, halo, trifluoromethyl, cyano, carboxy, carbamoyl, amino or $C_1$-$C_4$ alkoxycarbonyl; or ⊕R⁸ is pyridinium substituted on the adjacent carbon atoms with a divalent alkylene group represented by the formula $(-CH_2-)_q$ where q is 3, 4 or 5, or the divalent alkylene group is interrupted by an oxygen, sulfur or one or two nitrogen atoms and in addition can contain one or two double bonds and can be substituted in either ring by one or two of the same or different substituents selected from the groups defined above when ⊕R⁸ is a substituted pyridinium;

or ⊕R⁸ is thiazolium or a thiazolium substituted by one or two of the same or different groups selected from among amino, $C_1$-$C_4$ alkyl, $C_1$-$C_4$ alkylthio, $C_1$-$C_4$ alkoxy or $C_1$-$C_4$ alkyl substituted by hydroxy, $C_1$-$C_4$ alkanoyloxy, $C_1$-$C_4$ alkylsulfonyloxy, halo, $C_1$-$C_4$ alkoxy, $C_1$-$C_4$ alkylthio or amino;

or ⊕R⁸ is thiazolium substituted on the adjacent carbon atoms with a divalent alkylene group represented by the formula $(-CH_2-)_q$ where q is 3,4 or 5.

3. A process of claim 1 for producing a compound of the formula I wherein the reactants are contacted in a non-basic solvent having a dielectric constant between about 0 and about 10.

4. A process of claim 1 for producing a compound of the formula I wherein the reactants are contacted in ethyl acetate or tetrahydrofuran.

5. A process of claim 2 for producing a compound of the formula I wherein A is hydrogen, halo, cyano, hydroxy, azido, C-C₆ alkyl, halo($C_1$-$C_6$)alkyl, cyano($C_1$-$C_6$)alkyl, $C_1$-$C_6$ alkylthio, $C_1$-$C_6$ alkoxy or trifluoromethanesulfonyloxy.

6. A process of claim 5 for producing a compound of the formula I wherein A is halo, halo($C_1$-$C_6$)alkyl, trifluoromethanesulfonyloxy or $C_1$-$C_6$ alkyl.

7. A process of claim 1 for producing a compound of the formula I wherein f is 1; and R⁹ and R¹⁰ combine to form a double bond.

8. A process of claim 7 for producing a compound of the formula I wherein Z is —S—.

9. A process of claim 8 for producing a compound of the formula I wherein A is hydrogen, halo, cyano, hydroxy, azido, $C_1$-$C_6$ alkyl, halo($C_1$-$C_6$)alkyl, cyano($C_1$-$C_6$)alkyl, $C_1$-$C_6$ alkylthio, $C_1$-$C_6$ alkoxy or trifluoromethanesulfonyloxy.

10. A process of claim 7 for producing a compound of the formula I wherein Z is —CH₂—.

11. A process of claim 10 for producing a compound of the formula I wherein A is hydrogen, halo, cyano, hydroxy, azido, $C_1$-$C_6$ alkyl, halo($C_1$-$C_6$)alkyl, cyano($C_1$-$C_6$)alkyl, $C_1$-$C_6$ alkylthio, $C_1$-$C_6$ alkoxy or trifluormethanesulfonyloxy.

12. A process of claim 1 for producing a compound of the formula I wherein f is 0; Z is —S—, —S(O)— or —SO$_2$—, $R^9$ is methyl, A is methyl and $R^{10}$ is hydrogen.

13. A process of claim 9 for producing a compound of the formula I wherein the reactants are contacted in a non-basic solvent having a dielectric constant between about 0 and about 10.

14. A process of claim 9 for producing a compound of the formula I wherein the reactants are contacted in ethyl acetate or tetrahydrofuran.

15. A process of claim 11 for producing a compound of the formula I wherein the reactants are contacted in a non basic solvent having a dielectric constant between about 0 and about 10.

16. A process of claim 11 for producing a compound of the formula I wherein the reactants are contacted in ethyl acetate or tetrahydrofuran.

17. A process of claim 12 for producing a compound of the formula I wherein the reactants are contacted in a non-basic solvent having a dielectric constant between about 0 and about 10.

18. A process of claim 12 for producing a compound of the formula I wherein the reactants are contacted in ethyl acetate or tetrahydrofuran.

* * * * *